(12) United States Patent
Goodwin et al.

(10) Patent No.: US 7,524,881 B2
(45) Date of Patent: Apr. 28, 2009

(54) PRODUCTION OF Δ 9 TETRAHYDROCANNABINOL

(75) Inventors: Neil John Goodwin, Edinburgh (GB); Nicolas James Archer, Edinburgh (GB); Christopher Murray, Edinburgh (GB); Alan Kenneth Greenwood, Herts (GB); Derek Mchattie, Herts (GB)

(73) Assignee: Resolution Chemicals Limited, Stevenage, Hertfordshire (GB)

( * ) Notice: Subject to any disclaimer, the term of this patent is extended or adjusted under 35 U.S.C. 154(b) by 253 days.

(21) Appl. No.: 10/503,082

(22) PCT Filed: Feb. 3, 2003

(86) PCT No.: PCT/GB03/00441

§ 371 (c)(1), (2), (4) Date: Mar. 31, 2005

(87) PCT Pub. No.: WO03/064407

PCT Pub. Date: Aug. 7, 2003

(65) Prior Publication Data

US 2005/0171361 A1    Aug. 4, 2005

(30) Foreign Application Priority Data

Feb. 1, 2002  (GB) .................................. 0202396.8
Jun. 18, 2002 (GB) .................................. 0214022.6

(51) Int. Cl.
*A61K 31/352* (2006.01)
*C07D 311/72* (2006.01)

(52) U.S. Cl. ....................... 514/454; 549/388
(58) Field of Classification Search .................. 549/388; 514/454
See application file for complete search history.

(56) References Cited

U.S. PATENT DOCUMENTS 5,859,293 A    1/1999    Bailey et al.

FOREIGN PATENT DOCUMENTS

WO    WO 00/25127    5/2000

OTHER PUBLICATIONS

Ndjoko et al., Chromatographia (1998) vol. 47(1/2), pp. 72-76.*
British Search Report for British Application No. GB 0202396.8, UK Patent Office, United Kingdom, searched on Jul. 24, 2002.
Huffman, J.W., et al., "Regioselective Synthesis of (±)-11-Nor-9-carboxy-$\Delta^9$-THC," *J. Org. Chem.* 54:4741-4743, American Chemical Society (1989).
Huffman, J.W., et al., "Synthesis of (±)-11-Nor-9-carboxy-$\Delta^9$-tetrahydrocannabinol: New Synthetic Approaches to Cannabinoids," *J. Org. Chem.* 56:1481-1489, American Chemical Society (1991).
International Search Report for International Application No. PCT/GB 03/00441, European Patent Office, Netherlands, mailed on Aug. 18, 2003.
Kachensky, D.F., and Hui, R.A.H.F., "Preparation of Racemic, (−)- and (+) -11-Nor-$\Delta^9$-Tetrahydrocannabinol-9-carboxylic Acid," *J. Org. Chem.* 62:7065-7068, American Chemical Society (1997).
Mechoulam, R., and Gaoni, Y., Hashish-IV: The Isolation and Structure of Cannabinolic, Cannabidiolic and Cannabigerolic Acids, *Tetrahedron* 21:1223-1229, Pergamon Press Ltd. (1965).
Mechoulam, R., and Gaoni, Y., "Recent Advances in the Chemistry of Hashish, " *Fortschr. Chem. Org. Naturst.* 25:175-213, Springer Verlag (1967).
Smith, M.V., "Marijuana: THC and Analogs, " in *Psychedelic Chemistry*, Loompanics Unlimited, Port Townsend, WA, Chapter 2 (1984), http://www.rhodium.ws/chemistry/psychedelicchemistry/chapter2.html, accessed Jul. 17, 2002.
Verwey, A.M.A., and Witte, A.H., "A Rapid Method of Preparation of $\Delta^1$-THC by Isolation of $\Delta^1$-THC Acid from Hashish, " *Pharm. Weekbl.* 107:415-416, D B Centens Witgeversmij (1972).

* cited by examiner

*Primary Examiner*—Taofiq A Solola
(74) *Attorney, Agent, or Firm*—Sterne, Kessler, Goldstein & Fox P.L.L.C.

(57) ABSTRACT

Δ9 THC acid is obtained from plant material and extracted into an aqueous solvent under conditions of pH control. The acid is converted to a salt and the salt extracted into a polar solvent, yielding acid of high purity. The Δ9 THC acid is then converted to Δ9 THC which is further purified and combined with a carrier for pharmaceutical use.

11 Claims, 2 Drawing Sheets

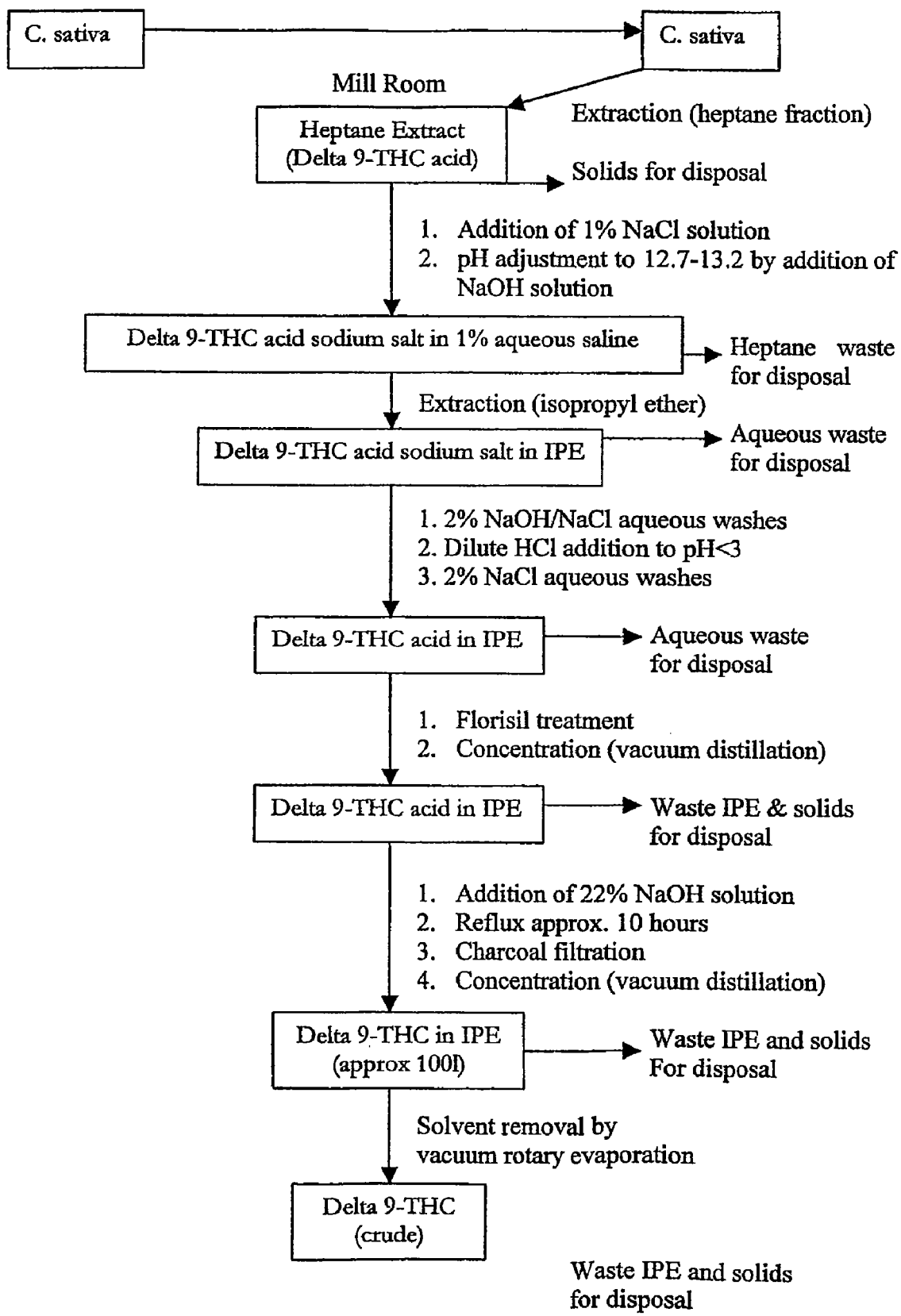

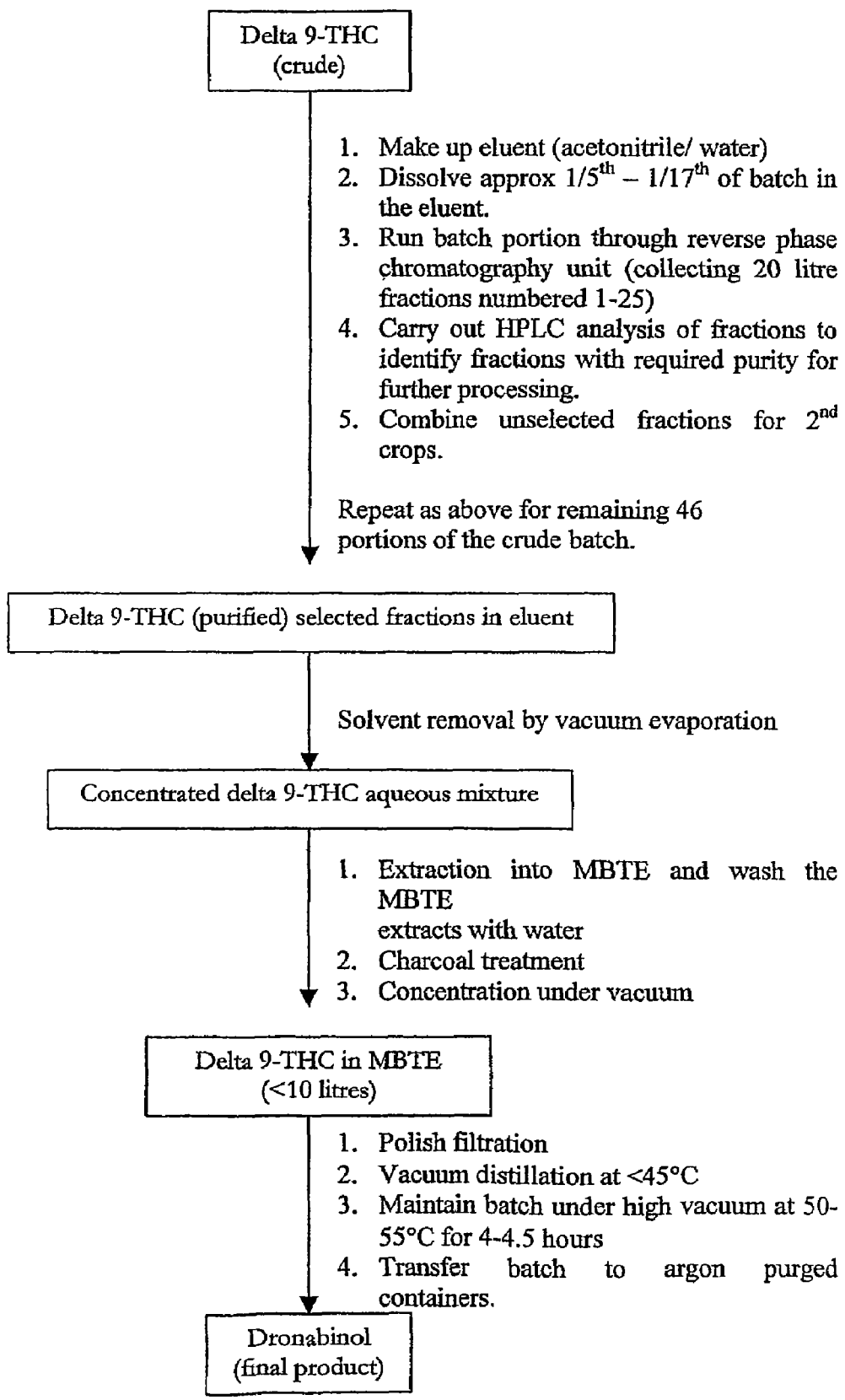
Figure 2 – Delta 9 THC Purification

PRODUCTION OF Δ 9 TETRAHYDROCANNABINOL

The present invention relates to the production of Delta 9 tetrahydrocannabinol (Δ9 THC), in particular to methods of its extraction from plant material and its purification, and also to compositions and pharmaceutical compositions containing the extracted and purified Δ9 THC.

Cannabinoids are a family of naturally occurring $C_{21}$ terpenophenolic compounds uniquely produced in cannabis. Marijuana usually refers to a mixture of leaves and flowering heads of the pistillate plant of *Cannabis sativa* from which tetrahydrocannabinols (THCs) are isolated. THCs contain two main isomeric forms, depending on the position of the double bond. The position of the double bond and the stereochemistry of these THCs have been confirmed by nuclear magnetic resonance and X-ray structure.

THCs have been used as psychomimetic agents for many years with the main psychomimetic activity being attributed to Δ9-THC (20 times greater than Δ8-THC). Δ9-THC is marketed as Marinol and is prescribed for patients suffering from severe nausea and vomiting associated with cancer chemotherapy.

The major cannabinoids present in cannabis other than Δ9- and Δ8-THC are cannabinol (CBN), cannabidiol (CBD) and Δ9-THC carboxylic acid which exists in two forms depending on the position of the carboxylate group. Cannabidiol (CBD) may be present in cannabis in large amounts but has little activity.

The major component of cannabis is Δ9-THC carboxylic acid which exists as two isomeric forms, THCA-A and THCA-B, both of which are psychomimetically inactive. It can be converted into the predominantely active constituent Δ9-THC, slowly on storage and rapidly on exposure to heat (e.g. when smoked). In fresh, dried marijuana, 95% of cannabinoids are present as THCA-A. THCA-A is less polar than THCA-B due to hydrogen bonding, between the hydroxy and carboxylate groups. Only THCA-A can readily be decarboxylated to Δ9-THC due to the presence of hydrogen bonding.

It is known to extract active ingredients from cannabis plant material using ethanol or a mixture of ethanol and water. The extract typically contains large amounts of Δ9-THC and Δ9 9 THC carboxylic acid and the acid is converted to Δ9 THC by refluxing the cannabis extract in ethanol. Δ9-THC is then purified.

A number of difficulties exist in this extraction and purification process.

First, the USP specification for pharmaceutical compositions containing Δ9 THC, referred to as dronabinol, indicates a maximum contaminant level of cannabinoids. The step of extracting active ingredients from cannabis routinely extracts a number of impurities which are difficult to remove from the finished product, and hence a large number of purification steps, including expensive column chromatography, are required to meet the USP requirements.

The existing method relies upon a distillation/reflux step to convert acid into active ingredient. This step is carried out at a high temperature under low vacuum, is rather time consuming and leads to some loss of active ingredient.

When active ingredient is extracted, plant material inevitably forms a component of the extract, which as a result has a tarry consistency and is difficult to handle. Also, the tarry plant material has to be removed otherwise it can severely hinder subsequent purification steps.

Other methods of extracting THC from plant material are also known. Where THC content of the plant material is high, the plant material is heated to decarboxylate the THC. Where THC content of the plant material is low, the inactive cannabidiolic acid is extracted with petroleum ether or benzene under alkaline conditions (pH 13.9) in the presence of sodium sulphite, acidfied and extracted with ether/chloroform. A problem with use of an undefined solvent such as petroleum ether is the lack of processing control and, as a consequence, high levels of impurities. The mixture of cannabidiolic acids thus obtained is then esterified and decarboxylated under alkaline conditions.

Tetrahedron (1965) vol. 21, pgs, 1223-1229 describes extacton from hashish using petroleum ether under alkaline conditions (pH 13.5). A crude mixture of THC-acids is extracted using ether/chloroform. A problem associated with extraction of the THC-acids into ether is that impurities, in particular Cannabidiol, are extracted together with the acid. The THC-acids are then esterified and Cannabinolic acid methyl ester is decarboxylated by heating under alkaline conditions to produce THC.

Pharm. Weekblad (1972) vol. 107, pgs 415-416 also describes extraction from hashish using hexane at pH 13.5. The extraction method used produces three layers—the hexane and aqueous layers being separated by a middle oily layer containing, inter alia, cannabinoid acids. This middle oily layer contains contaminants such as Cannabidiol and forms a sticky gum, which has a tendency to adhere to the walls of the separator, making phase separation difficult. The oily and aqueous layers are combined and extracted using diethylether. A silica gel column is subsequently used to remove plant material.

BRIEF SUMMARY OF THE INVENTION

It is therefore an object of the present invention to provide an alternative method for production of Δ9 THC, including an alternative extraction method and an alternative purification method, that ameliorates the difficulties in the art. An object of a specific embodiment of the invention is to provide a production method with increased yield and/or decreased impurities in the final product. A further object of a specific embodiment of the invention is to provide an improved production method with fewer and/or simpler steps to the final product.

DETAILED SUMMARY OF THE INVENTION

Accordingly, the present invention provides a method of production of Δ9 THC in which Δ9 THC carboxylic acid is extracted from plant material then converted to Δ9 THC, and active ingredient is obtained having a lower level of contamination than hitherto. Preferably, the Δ9 THC carboxylic acid is purified prior to being decarboxylated, the purified material requiring fewer further steps to obtain product meeting the USP requirements.

In a first aspect of the invention, a method for production of Δ9 THC comprises extracting Δ9 THC and Δ9 THC carboxylic acid from plant material, forming a salt of Δ9 THC carboxylic acid and extracting the salt using a solvent, wherein the solvent preferentially dissolves the salt compared to Δ9 THC.

An advantage of the invention is that cannabinol and cannabidiol, major contaminants of prior art preparations, tend to exhibit the solubility profile of Δ9 THC. Hence, the use of a solvent that preferably dissolves a salt of Δ9 THC carboxylic acid, compared to Δ9 THC extracts the majority of the Δ9 THC carboxylic acid (as a salt) but preferentially leaves behind these contaminants. Δ9 THC is also left behind by this extraction, but as Δ9 THC for only a minor component of the extractable substances of interest, this can be sacrificed so that the initially extracted product has acid of improved purity which can in turn be converted to Δ9 THC of improved purity or can be converted to Δ9 THC of acceptable purity with fewer steps. A particularly suitable solvent for this extraction is a basic aqueous solution.

The solvent for initial extraction of Δ9 THC and its acid from plant material is suitably a non-polar solvent or a mixture of non-polar solvents, with alkanes as described below being particularly suitable as solvent components. A number of non-polar solvents are suitable for the extraction, and these solvents include straight and branched alkanes, in particular pentane, hexane, heptane, octane, and nonane, other petrol fractions and other solvents immisible with water. In an example of the invention set out in detail below, particularly good results have been obtained using heptane.

A further advantage of the present invention is that the use of these non-polar solvents tends to result in an extract that contains very much reduced levels of plant material compared to the prior art extract. Subsequent processing of the extract to remove residual plant material is thus facilitated. The extract is furthermore, less tarry and easier to handle than the prior art extracts.

In another method of a first aspect of the invention Δ9 THC and its acid are extracted, from plant material and the first extraction step is followed by a further step in which the Δ9 THC carboxylic acid is converted into a derivative which is itself extracted with a second solvent. This further step confers the advantage that contaminants that were extracted with the first solvent, typically a non-polar solvent such as an alkane, do not extract into the second solvent which is typically a polar solvent, and hence further purification of the acid is achieved. Good results have been obtained, for example, by carrying out a second extraction using an aqueous solvent and a derivative that preferentially dissolves in the aqueous phase compared with the first extraction solvent. The derivative can then be converted back into Δ9 THC carboxylic acid or can be converted into Δ9 THC. A salt of Δ9 THC carboxylic acid is used in an embodiment of the invention, as this extracts efficiently into a basic aqueous phase.

In a second aspect of the invention there is provided a method of production of Δ9 THC from plant material that contains both Δ9 THC and Δ9 THC carboxylic acid, comprising separating the plant material into at least first and second fractions, said first fraction containing a major amount of the Δ9 THC from the plant material and said second fraction containing a major amount of the Δ9 THC carboxylic acid from the plant material, and discarding the first fraction whilst retaining the second fraction.

In the initial fractionation Δ9 THC is in whole or part lost but the retained Δ9 THC carboxylic acid is obtained with a low level of impurities and its subsequent purification is straightforward and results in a highly pure end-product. When solvent extraction is used in such a method, the first fraction is located within the organic solvent extract of the plant material and the second fraction is located within the aqueous extract.

In use of the invention as described below in more detail, the method purifies the Δ9 THC carboxylic acid and then converts the purified acid to Δ9 THC. The chemistry of purifying the acid has been found to be non-complicated and can be carried out so as to obtain acid of high purity, typically at least 90% or greater by weight of cannabinoids.

The present invention hence provides a new chemical route to purified Δ9 THC not contemplated in the art, via extracting Δ9 THC carboxylic acid from plant material using a first solvent, converting the Δ9 THC carboxylic acid to a salt and extracting that salt with a second solvent. It is a benefit of adopting a purification going through a salt of the Δ9 THC carboxylic acid that the different chemical solubility of the acid and the salt can be used to increase the purity of the end product or at least to simplify the steps required to achieve that level of purity.

In an example of the invention in operation, Δ9 THC carboxylic acid is extracted from cannabis plant material using a first solvent which is a non-polar solvent or a mixture of non-polar solvents, converted into a salt and then the salt is extracted from the first solvent using a second, aqueous solvent. Contaminating substances that extract into the non-polar solvent from the starting plant material tend not to then be extracted into the aqueous phase. The conversion of the salt back into acid is straightforward. In an example, the Δ9 THC carboxylic acid is converted to a sodium acid addition salt, though salts of magnesium, lithium or potassium can also be used. Strongly alkaline pH, suitably pH 12-14, especially about pH 12.5-13.5, is used to make the salt. It is also found that an agent to reduce emulsion formation may be employed—sodium chloride in the example though others will be suitable.

The Δ9 THC carboxylic acid addition salt needs to be converted to Δ9 THC and this is usually done by decarboxylating the salt, preferably at elevated temperature. In a particular embodiment of the invention the salt is extracted into a third solvent, further purified and then decarboxylation is carried out in the third solvent, and this has the advantage that no solvent swap is needed before decarboxylation. Preferably, the decarboxylation is carried out in the presence of an alkaline solution, typically a basic aqueous solution.

Δ9 THC carboxylic acid and Δ9 THC can both be susceptible to oxygenation during the purification process, and therefore it is preferred to carry out the methods in an inert gas atmosphere. Nitrogen is suitable.

The purified Δ9 THC can further be treated to remove cannabinoids using diatomaceous earth prior to being stored ready for further processing.

In use of the invention, Δ9 THC acid is extracted, purified and then converted into the active ingredient Δ9-THC in a multi-step process. In a preferred example of the production method, *Cannabis sativa* (leaf and flowering head) is milled until homogeneous then extracted at ambient temperature (15-25° C.) with heptane. The heptane fraction extract obtained contains a mixture of cannabinoids, the main component being Δ9-tetrahydrocannabinol carboxylic acid (Δ9-THC aid). The Δ9-THC acid is extracted as its sodium salt into a dilute sodium chloride/sodium hydroxide solution, then the salt is subsequently extracted in to isopropyl ether (IPE). The Δ9-THC acid sodium salt, unexpectedly, dissolves better in IPE than in the basic aqueous solution and hence extracts into the IPE from the basic aqueous phase. This step is not seen in known methods in the art, which extract the acid into ether or diethylether. Extraction of the salt into IPE has the added, surprising, advantage of allowing a further improvement in purification, since impurities (in particular Cannabidiol) remain in the aqueous phase while the Δ9-THC acid sodium salt extracts into the IPE. The Δ9-THC acid sodium salt in IPE is washed with a 2% w/v aqueous sodium hydroxide/sodium chloride solution, then acidified (pH<3) with dilute hydrochloride acid. Hence, the present invention comprises the steps of extracting the salt into a third solvent, optionally washing, followed by acidification. In contrast, the art methods acidify prior to extracting into ether, resulting in less efficient purification.

The third solvent is suitably a polar solvent. Good results have been obtained using IPE though other polar solvents including diethyl ether dimethyl ether and other ethers, chloroform, as well as mixtures of such solvents, can also be used.

In one specific extraction the composition of the IPE—extracted salt was measured as 96.4% salt, 0.5% CBD and 0.8% CBN, demonstrating the high purity following this salt-extraction step.

The Δ9-THC acid solution can conveniently be treated by passing through a florisil bed, to remove plant material, which is insoluble in IPE. Acidification of the Δ9-THC acid sodium salt is required prior to florisil treatment because salt will not pass through the bed. The Δ9-THC acid solution in IPE is then decarboxylated by refluxing the solution in the presence of 22% aqueous sodium hydroxide solution for approximately 10 hours. Reaction completion is confirmed by HPLC analysis. The resultant Δ9-THC is charcoal treated in IPE then concentrated to isolate Δ9-THC (crude). Δ9-THC (crude) is stored at −20° C. prior to purification.

The above-described embodiments hence enable production of relatively crude, by pharmacological standards, preparations of Δ9 THC. For use in a pharmaceutical composition additional purification will generally be needed. Final purification of Δ9-THC is suitably performed using a medium pressure chromatography unit. Five to seven column operations per batch are carried out on a 33 kg pre packaged reverse phase (C18 Hypersil) cartridge using an isocratic eluent system of acetonitrile/water to produce a single batch of Dronabinol. The combined fractions of suitable purity after chromatography are concentrated, extracted into methyl-butyl ether (MTBE), charcoal treated and finally distilled under high vacuum at 50-55° C. until the residual solvent is <5000 ppm (4-4½ hours). The final product is a viscous oil below ambient temperature which is stored under an inert atmosphere (argon) in PTFE or amber glass containers below −20° C.

Accordingly, a further aspect of the invention lies in a method of purification of Δ9 THC, comprising measuring a level of cannabinol in a Δ9 THC-containing composition and if the level is above a predetermined threshold then treating the composition to further purify the Δ9 THC and repeating the method. Generally, a cannabinol level of 0.5% or greater is unacceptable, and product preferably containing 0.3% and more specifically 0.2% or less cannabinol, meets the criteria for passing on to later processing steps.

A feature of the invention is the purity of product obtained, and the purification is typically carried out on a Δ9 THC-containing composition in which the Δ9 THC has a minimum purity of 85% by weight, even of 90% by weight, most preferably of 98% by weight, due to the purity achievable by the production methods according to earlier aspects of the invention.

Preferred further purification steps include charcoal filtration and reverse phase chromatography to purify the Δ9 THC, with typical result being Δ9 THC of 98% or 99% by weight purity or greater, most preferably of 99.5% by weight purity.

End purified Δ9 THC can then be combined with a pharmaceutically acceptable carrier.

Still further aspects of the invention lie in the products and intermediates obtained according to the methods disclosed. Thus the invention also provides purified Δ9 THC having a purity of at least 95% by weight, preferably at least 98% by weight, more preferably at least 99% by weight, most preferably at least 99.5% by weight, optionally in combination with a pharmaceutically acceptable carrier.

The invention also provides a Δ9 THC carboxylic acid salt, preferably one that is at least 75% pure by weight, more preferably at least 90% pure by weight, most preferably at least 95% pure by weight. This salt can be dissolved in a solvent in a further composition of the invention. Further compositions of the invention are an aqueous solution of the salt, wherein the salt is at least 75%, preferably at least 90% and more preferably at least 95% pure by weight.

A yet further aspect of the invention provides Δ9 THC carboxylic acid of at least 85% by weight purity, preferably at least 90% by weight purity, most preferably at least 95% by weight purity. The acid can be in the form of an oil or can be dissolved in aqueous, or non-aqueous solutions.

In a further specific embodiment of the invention, described in detail in an example below, cannabis plant is milled and then Δ9-THC carboxylic acid is extracted therefrom using heptane. Residual solid material is then disposed of. To the heptane extract is added an aqueous solution of sodium chloride and the pH is adjusted to about 13, typically from 12.7 to 13.2, by addition of sodium hydroxide solution. Hence, the sodium salt of Δ9-THC carboxylic acid is made. The use of sodium chloride helps to avoid emulsion formation during this process. Tight pH control is necessary to ensure efficient extraction, especially when the process is scaled up. When a pH within the range 12.7-13.2 is used, the formation of 2 layers is observed—a lower aqueous layer and an upper organic layer containing contaminants, which is discarded. In contrast, known methods use very alkaline pH (typically in the pH range 13.5-13.9), resulting in formation of a 3-layer system, with the Δ9-THC acid salt "oiling out" between the organic and aqueous layers. This causes processing problems during subsequent phase separations. We have found that use of such high pH may also lead to degradation and decarboxylation of the desired THC-acid, thus reducing yield of Δ9-THC. We have also found that if, however, too low a pH is used (typically below pH 12.7) then there will be incomplete extraction of the Δ9-THC acid salt and high levels of the contaminant Cannabidiol in the aqueous phase. Hence, generally, extraction of the Δ9-THC acid into the aqueous phase from the first solvent is preferably carried out at pH 12.7-13.2.

Conversion of the acid into its sodium salt means that the Δ9-THC salt now preferentially dissolves in the aqueous phase. Thus, a further purification is achieved because contaminants that dissolved in the heptane fraction remain in that fraction, whereas the desired material now passes into the aqueous phase. Hence, the next stage is that the heptane phase is discarded.

The Δ9 THC acid sodium salt is then extracted using isopropyl ether, with the aqueous phase discarded. The isopropyl ether is then subjected to aqueous washes containing sodium hydroxide and sodium chloride, dilute hydrochloric acid is added to lower the pH to 3 or below and further washes using aqueous sodium chloride are carried out, which have the result that the acid sodium salt is converted back into Δ9 THC acid. The aqueous waste is discarded. The Δ9 THC acid is then subjected to florisil treatment to remove plant material and concentrated by vacuum distillation. The Δ9 THC acid in isopropyl ether then has sodium hydroxide solution added and the whole mixture is refluxed to achieve decarboxylation to Δ9 THC. This is then filtered through charcoal and concentrated using vacuum distillation. Next, the solvent is removed by vacuum, resulting in crude Δ9 THC.

The next stage is purification of the crude product. In the specific embodiment set out below, the crude product is filtered through charcoal to remove cannabinoids and if the cannabinol level is satisfactory, that is to say 0.2% or less by weight, the product having this level of cannabinol is subjected to further purification steps resulting in the final purified product which typically has a Δ9 THC level of 95% plus, or typically 97% plus and often as high as 99% plus by weight, most preferably 99.5% by weight. This is combined with sesame seed oil in soft gelatine capsules to give the end product known as Dronabinol.

A yet further aspect of the invention provides a method of production of Δ9 THC by solvent extraction of plant material, wherein the solvent extraction is carried out using a non-polar solvent or a mixture of non-polar solvents. The hitherto known methods used such solvents as water and ethanol and mixtures of the same, extracting active ingredients but also plant material at the same time. Use of a non-polar solvent reduces the plant content of the extract. Prior art extracts were tarry and difficult to process, and this is no longer the case when non-polar solvents are employed. Preferred solvents include straight or branched $C_5$-$C_9$ alkanes, and the solvents are preferably substantially free of water and substantially free of ethanol.

BRIEF DESCRIPTION OF THE DRAWINGS

The present invention is now illustrated in the following Examples, with reference to the accompanying drawings in which:

FIG. 1 is a flow diagram of the process of the present invention for production of crude Δ9 THC;

FIG. 2 is a flow diagram of the process of the present invention for converting the crude Δ9 THC into the final product.

EXAMPLES

Example 1

Selection of Plants

An analytical screening programme of *Cannabis sativa* was devised consisting of two phases.

Phase 1 involved the growing of 247 plants from seed and, after 4-6 weeks, analysis of leaf sections of the plants by GC for impurity profile and Δ9-THC content. Under the GC operating conditions all Δ9-THC carboxylic acid decarboxylates to Δ9-THC on the column. Based on the phase 1 analysis, a reduced number of plants were selected (24 in total) to progress to the next phase.

Phase 2 of the programme involved analysis of the 24 selected plants once flowering had begun. The individual flowering heads were ground and mixed thoroughly to obtain homogeneous material and analysis of the homogenised flowering heads was carried out in duplicate by GC.

Selection of the desired clone plant was carried out based on product yield and impurity profile.

Phase 1 of the selection process was undertaken over a 5 week period. Sample preparation and GC analytical methodology were according to a modified screening protocol.

This modified protocol reduced sonication time of leaf sections in ethanol from 30 minutes to 15 minutes and reduced centrifugation time from 15 minutes to 5 minutes. Analysis of the final extract using the modified protocol by GC revealed negligible Δ9-THC, indicating exhaustion of leaf using shorter processing times.

Initial GC analysis of cannabis leaf samples showed large variations in Δ9-THC content and Δ9-THC/Cannabidiol ratios (cannabidiol is the main cannabinoid impurity in the leaf). Samples injected in duplicate were found to be consistent.

Following selection of 24 plants, phase 2 analysis on homogeneous samples of flowering heads was conducted. Again a number of samples were injected in duplicate to ensure a representative analysis and reproducibility of the method. Large variations in the Δ9-THC content was evident ranging from 77.0 to 84.8% by GC area. There was also large differences in the impurity profiles from plant to plant. From the screening programme plant 397/92 was selected as the final clone.

Example 2

Extraction

This eraction is described with reference to FIG. 1.

Milling of *Cannabis Sativa*/Extraction with Heptane Fraction

*Cannabis sativa* (125 kg, leaf and flowering head) is milled using shredders. The milled material is then charged to a nitrogen purged vessel followed by hepatne fraction (1250 litres). The contents are stirred for 4-4 ½ hours under a low flow of nitrogen at ambient temperature (15-25° C.) then filtered. The filter cake is sucked dry for 30 minutes then the extracted plant material dug off the filter and recharged to the vessel. Heptane fraction (625 litres) is charged and the vessel contents stirred for 30 minutes at ambient temperature (15-25° C.) then filtered. Again the filter cake is sucked dry for 30 minutes. The heptane fraction extracts are combined.

pH Adjustment

A 1% w/v aqueous solution of sodium chloride is prepared (375 litres) and added to the vessel containing heptane fraction extract, and the vessel contents stirred for 10 minutes at ambient temperature (15-25° C.). 22% sodium hydroxide solution is then added in 1 litre portions until 6 litres has been added. The pH of the aqueous solution is tested by allowing the layers to settle. Further portions of 22% sodium hydroxide solution (100 ml) are added until the pH range is within the range pH 12.7-13.2. The contents are allowed to settle and the upper organic layer transferred to waste.

Solvent Washes/Extractions

The aqueous extract (~380 litres) is extracted with IPE (4×100 litres) and the combined IPE extract washed with a 2% w/v aqueous solution of sodium hydroxide/sodium chloride (3×390 litres) then acidified with 1N hydrochloric acid. The aqueous layer is allowed to settle and the pH checked to ensure a pH<3. The IPE extract is then water washed with 2% w/v aqueous solution of sodium chloride until the aqueous solution is pH>5.

Florisil Treatment

Florisil (60 kg) and IPE are stirred together to form a slurry and the slurry is transferred to a Nutche filter. The IPE extract is allowed to percolate through the florisil bed under gravity before vacuum is applied.

An IPE wash is then passed through the florisil bed and the florisil sucked dry under vacuum.

Batch Concentration

The combined IPE extract is concentrated under vacuum to approximately 300 litres ensuring the batch temperature is kept below 40° C.

Decarboxylation/Charcoal Treatment

Sodium hydroxide solution (22% w/w, S.G. 1.24) (100 litres) is charged to the vessel containing the IPE extract and the vessel contents stirred and heated under a gentle reflux for 10 hours. A low flow of nitrogen is passed over the vessel to limit oxidation during decarboxyation. The volume and vessel contents temperature are monitored regularly to ensure that the vessel volume does not reduce significantly and the vessel contents remains below 68° C. After 10 hours, the vessel contents are cooled and process water charged to the vessel. The contents are stirred at ambient temperature then the aqueous solution runs to waste. Activated carbon is added and the vessel contents stirred 30-40 minutes at ambient temperature. The vessel contents are polish filtered and concentrated to approximately 100 litres under vacuum ensuring the vessel contents remain below 45° C. The batch is cooled to <20° C. and transferred to 25 litre containers for final concentration.

Isolation of Δ9-THC (Crude)

The IP extract (~100 litres) is concentrated under vacuum on the buchi rotary evaporator ensuring the water bath temperature remains below 45° C. Once the vessel contents reach 8-10 litres the solution is transferred to a 20 litre jacketed vessel and concentrated under vacuum below 45° C. until no more solvent distils over. The vessel contents are then run at 55-60° C. into 3 litre glass containers purged with argon to give approximately 5×1 kg portions of Δ9-THC (crude). The contents are cooled to ambient temperature (15-25° C.) and purged under argon and stored below -20° C.

Example 3

This purification is described with reference to FIG. 2.

Purification of Δ9-THC (Crude)

Δ9-THC (crude) is removed from the freezer.

Column Chromatography/Charcoal Treatment/Final Batch Concentration

Δ9-THC (crude, ~1 kg portion) is dissolved in acetonitrile/water (60:40) (2 volumes) with sonication and transferred to the chromatography sample reservoir. The sample solution is then loaded onto the column and fractions collected. Fractions are analysed by HPLC, the column operation is repeated four to six times and fractions of relevant purity concentrated under vacuum, the temperature remaining between 40 and 45° C., to a third of the original volume. The vacuum is released with nitrogen before extracting Δ9THC into methyl t-butyl ether (MTBE). The resultant Δ9-THC solution is stirred with purified water at ambient temperature for 25-35 minutes. The aqueous layer is run to waste and the MTBE solution of Δ9-THC is treated with activated carbon. The solution is concentrated under vacuum with the temperature maintained at 35-45° C., then, once the volume is <10 litres, transferred through a polish filtration unit into a vessel set for distillation in the finishing room. The solvent is distilled under vacuum ensuring the batch temperature is below 45° C. Once all the solvent has distilled over the high vacuum pump is connected and the batch maintained at 50-55° C. at less than 10 mbar for 4-4½ hours. A sample is withdrawn for residual solvent analysis and once the levels are within the limit, the batch is transferred at 50-55° C. into argon purged containers. Once the transfer is complete the containers are purged with argon, sealed and stored below -20° C.

Results

Different batch runs were analysed by HPLC for Δ9 THC content after removal of residual solvent, and showed a Δ9 THC content of 99.3% (cannabinol—0.2%, other impurities—0.5%, all by peak area).

Example 4

Further Method for Purification of Δ9-THC (Crude)

The column (Flash 75 L, 1,200 g C18 on silica) was washed with 8 litres of 99% methanol, 4 litres 50:50 methanol water and 8 litres of 75:25 methanol water before the first use. Crude THC 0005 (~54 g) was dissolved in 30 ml of methanol with sonication, then 10 ml of water was added. The sample solution was loaded onto the column and eluted with 75% methanol 25% water (55 psi, 200 ml/min). A single large (8 or 12 litres) and 23-27 litre fractions were collected. Fractions were selected based on the HPLC traces (resolution or gradient methods).

Selected fractions were transferred to one of three 2 litre buchi flasks and the solvents removed under vacuum at 45-50 degrees C. NJG 197 was distilled over 2 days (13 hours) and 25 ml of methanol was added to each buchi before being held over the weekend at room temperature in the dark, NJG 198 was distilled over two days (10 hours) before being extracted. The aqueous concentrate from each experiment was transferred to a 5 litre separating funnel equipped with a overhead stirrer. MTBE (600 ml) was used to dissolve the oil remaining in the buchi flasks and the solution added to the separator. Sodium chloride (10 g) was added to the separator to reduce the amount of interfacial emulsion formed.

The mixture was stirred for 2 minutes, allowed to settle and the organic phase transferred to an amber bottle and flushed with nitrogen. The aqueous phase was then extracted with two 500 ml portions of MTBE. The organic extracts were combined and back washed with water (500 ml). The organic phase was then concentrated under works vacuum at 40-45 degrees C.

Flash 75 charcoal and concentration (NJG 200) The oils produced from the Flash 75 L experiments (NJG 197 and 198,51.6 g total) were dissolved in MTBE (150 ml) and combined. The solution was loaded onto a Flash 75 S charcoal column (acid activated and immobilised prewashed with 500 ml MTBE). The sample was eluted with pure MTBE (12 psi, 125 ml/min) can 250 ml fractions collected in amber bottles preflushed with nitrogen. Samples were analysed by the resolution and gradient HPLC method.

Fractions were selected on the basis of concentration and purity on the resolution system. The selected fractions (1,500 ml) were combined and concentrated in a foil wrapped buchi flask at 45 degrees C. under works vacuum. The oil was flushed with nitrogen and stored in the freezer overnight (2 h 40 minutes after the sample was loaded onto the column).

The following day the oil was sampled for gradient HPLC analysis and dried under high vacuum (<10 mbar) at 45-50 degrees C. for 4 hours.

RESULTS

Different batch runs were analysed by HPLC for Δ9 THC content after removal of residual solvent, and showed a Δ9 THC content of 99.7%

The invention thus provides methods for production and purification of Δ9 THC.

The invention claimed is:

1. A method of purification comprising charcoal filtration of a Δ9 THC containing composition with a minimum purity of at least 85% by weight Δ9 THC before filtration so as to obtain a purified Δ9THC containing composition wherein the Δ9THC containing composition is obtained by extracting Δ9THC carboxylic acid from plant material using a solvent and converting the Δ9THC carboxylic acid to Δ9THC, and wherein charcoal filtration removes cannabinoids from the Δ9THC containing composition.

2. The method of claim 1, wherein the charcoal filtration is conducted in methyl t-butyl ether.

3. The method of claim 1, further comprising reverse phase column chromatography.

4. The method claim 3, wherein the chromatography is carried out on a C18 Hypersil™ cartridge using an isocratic eluent system of acetonitrile/water.

5. The method of claim 3, comprising purification by reverse phase column chromatography followed by treatment with charcoal.

6. The method of claim 3, wherein the Δ9 THC containing composition contains 98% Δ9 THC by weight purity or greater.

7. The method of claim 3, wherein the Δ9 THC containing composition contains 99% Δ9 THC by weight purity or greater.

8. The method of claim 3, wherein the Δ9 THC containing composition contains 99.5% Δ9 THC by weight purity or greater.

9. The method of claim 3, further comprising combining pyrified Δ9-THC with a pharmaceutically acceptable carrier.

10. The method of claim 9, wherein the Δ9 THC is combined with sesame seed oil in soft gelatine capsules.

11. The method of claim 1 wherein the purified Δ9 THC containing composition contains 0.3% cannabinol by weight or less.

* * * * *